United States Patent [19]

King

[11] Patent Number: 4,937,247

[45] Date of Patent: Jun. 26, 1990

[54] 1-ACYL INDAZOLES

[75] Inventor: Francis D. King, Harlow, England

[73] Assignee: Beecham Group p.l.c., Brentford, England

[21] Appl. No.: 101,081

[22] Filed: Sep. 25, 1987

Related U.S. Application Data

[63] Continuation-in-part of Ser. No. 856,452, Apr. 25, 1986, abandoned.

[30] Foreign Application Priority Data

| Apr. 27, 1985 | [GB] | United Kingdom | 8510752 |
| Oct. 21, 1985 | [GB] | United Kingdom | 8525913 |
| Sep. 26, 1986 | [GB] | United Kingdom | 8623142 |

[51] Int. Cl.$^5$ .............. C07D 451/12; C07D 451/14; A61K 31/36; A61K 31/435
[52] U.S. Cl. .................. 514/299; 514/212; 514/304; 546/112; 546/126; 540/603
[58] Field of Search ............ 546/112, 126; 514/299, 514/304, 603, 212

[56] References Cited

FOREIGN PATENT DOCUMENTS

| 0200444 | 11/1986 | European Pat. Off. | 546/112 |
| 02223385 | 5/1987 | European Pat. Off. | 546/126 |
| 8400166 | 1/1984 | PCT Int'l Appl. | 546/126 |
| 8501048 | 3/1985 | PCT Int'l Appl. | 546/126 |
| 8502847 | 7/1985 | PCT Int'l Appl. | 546/112 |
| 2152049 | 7/1985 | United Kingdom | 546/112 |

OTHER PUBLICATIONS

King, Chem. Abstrats, vol. 109(9) 109:73, 453-d, Aug. 29, 1988.

*Primary Examiner*—Alan L. Rotman
*Attorney, Agent, or Firm*—James F. Haley, Jr.; David K. Barr; Emily A. Evans

[57] ABSTRACT

Compounds of formula (I) and pharmaceutically acceptable salts thereof:

wherein
X is CH or N;
Y is NH or O;
$R_1$ is hydrogen or halogen;
$R_2$ is a group of formula (a), (b) or (c)

wherein n is 2 or 3; p and q are independently 1 to 3; and $R_4$ or $R_5$ is $C_{1-4}$ alkyl;
$R_3$ is $C_{1-10}$ acyl, $C_{1-6}$ alkoxycarbonyl, optionally substituted phenoxycarbonyl or benzyloxycarbonyl, or $R_6R_7NCO$ or $R_6R_7NS(O)_m$ wherein m is 1 or 2 and $R_6$ and $R_7$ are independently $C_{1-6}$ alkyl groups or together are $C_{4-6}$ polymethylene; having 5-HT$_3$ antagonist activity, a process for their preparation and their use as pharmaceuticals.

10 Claims, No Drawings

1-ACYL INDAZOLES

This is a continuation-in-part of application Ser. No. 856,452, filed Apr. 25, 1986, now abandoned.

This invention relates to novel compounds having useful pharmacological properties, to pharmaceutical compositions containing them, to a process and intermediates for their preparation, and to their use as pharmaceuticals.

UK patent applications, GB Nos. 2100259A and 2125398A describe esters and amides having an azabicyclic side chain and possessing 5-HT$_3$ (5-Hydroxytryptamine) antagonist activity.

A class of novel, structurally distinct compounds has now been discovered. These compounds have 5-HT$_3$ antagonist activity and/or gastric motility enhancing activity.

Accordingly, the present invention provides a compound of formula (I), or a pharmaceutically acceptable salt thereof:

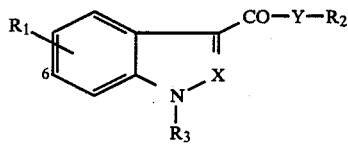

wherein
X is CH or N;
Y is NH or O;
R$_1$ is hydrogen or halogen;
R$_2$ is a group of formula (a), (b) or (c)

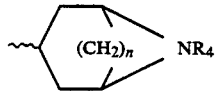

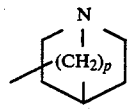

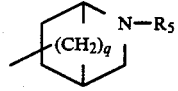

wherein n is 2 or 3; p and q are independently 1 to 3; and
R$_4$ or R$_5$ is C$_{1-4}$ alkyl;
R$_3$ is C$_{1-10}$ acyl; C$_{1-6}$ alkoxycarbonyl, optionally substituted phenoxycarbonyl or benzyloxycarbonyl, or R$_6$R$_7$NCO or R$_6$R$_7$NS(O)$_m$ wherein m is 1 or 2 and R$_6$ and R$_7$ are independently C$_{1-6}$ alkyl groups or together are C$_{4-6}$ polymethylene.

Values for R$_1$ include hydrogen, fluoro, chloro and bromo. R$_1$ is often hydrogen or 5-halo, such as 5-fluoro or 5-chloro.

Preferably R$_1$ is hydrogen.
Preferably p and q are 1 or 2.
Suitable values for R$_4$/R$_5$ include as groups of interest, C$_{1-3}$ alkyl such as methyl, ethyl and n- and iso-propyl.

R$_4$/R$_5$ is preferably methyl or ethyl, most preferably methyl.

In R$_3$:

Examples of alkoxycarbonyl groups include methoxy-, ethoxy-, n- and iso- propoxycarbonyl, or phenoxycarbonyl or benzyloxycarbonyl optionally substituted in the phenyl ring by one or two substituents selected from C$_{1-4}$ alkyl, C$_{1-4}$ alkoxy, trifluoromethyl, halogen or nitro.

Examples of acyl groups include C$_{1-6}$ alkanoyl, for example acetyl, propionyl, n- and iso-butyl, 2,3-dimethylpropanoyl, and benzoyl or benzenesulphonyl either being optionally substituted in the phenyl ring by one or two substituents selected from C$_{1-4}$ alkyl, C$_{1-4}$ alkoxy, trifluoromethyl, halogen or nitro, or sulphonyl groups, for example a C$_{1-6}$ alkylsulphonyl group, such as methanesulphonyl.

Examples of R$_3$ when R$_6$R$_7$NCO or R$_6$R$_7$S(O)$_m$ include, as values for R$_6$ and R$_7$, methyl, ethyl, n- and iso-propyl, or R$_6$ and R$_7$ together are C$_4$, C$_5$ or C$_6$ polymethylene. R$_6$ and R$_7$ are often both methyl.

R$_3$ is often acetyl.

The pharmaceutically acceptable salts of the compounds of the formula (I) include acid addition salts with conventional acids such as hydrochloric, hydrobromic, boric, phosphoric, sulphuric acids and pharmaceutically acceptable organic acids such as acetic, tartaric, maleic, citric, succinic, benzoic, ascorbic, methanesulphonic, α-keto glutaric, α-glycerophosphoric, and glucose-1-phosphoric acids.

The pharmaceutically acceptable salts of the compounds of the formula (I) are usually acid addition salts with acids such as hydrochloric, hydrobromic, phosphoric, sulphuric, citric, tartaric, lactic and acetic acid.

Preferably the acid addition salt is the hydrochloride salt.

Examples of pharmaceutically acceptable salts include quaternary derivatives of the compounds of formula (I) such as the compounds quaternised by compounds R$_{10}$-T wherein R$_{10}$ is C$_{1-6}$ alkyl, phenyl-C$_{1-6}$ alkyl or C$_{5-7}$ cycloalkyl, and T is a radical corresponding to an anion of an acid. Suitable examples of R$_{10}$ include methyl, ethyl and n- and iso-propyl; and benzyl and phenethyl. Suitable examples of T include halide such as chloride, bromide and iodide.

Examples of pharmaceutically acceptable salts of the compounds of formula (I) also form internal salts such as pharmaceutically acceptable N-oxides.

The compounds of the formula (I) and their pharmaceutically acceptable salts, (including quaternary derivatives and N-oxides) may also form pharmaceutically acceptable solvates, such as hydrates, which are included whenever such compounds and salts are herein referred to.

It will of course be realised that some of the compounds of the formula (I) have chiral or prochiral centres and thus are capable of existing in a number of stereoisomeric forms including enantiomers. The invention extends to each of these stereoisomeric forms (including enantiomers), and to mixtures thereof (including racemates). The different stereoisomeric forms may be separated one from the other by the usual methods.

When R$_2$ is of formula (a) the compound of formula (I) may exist as an endo or exo isomer, the endo isomer of which is preferred.

A group of compounds within formula (I) is of formula (II):

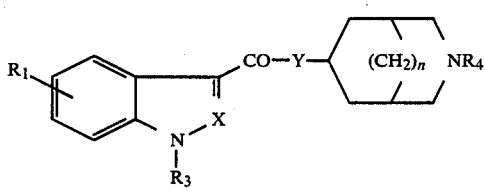

(II)

wherein the variables are as defined in formula (I).

Examples of the variables and preferred variables are as so described for corresponding variables in relation to formula (I).

A further group of compounds within formula (I) is of formula (III):

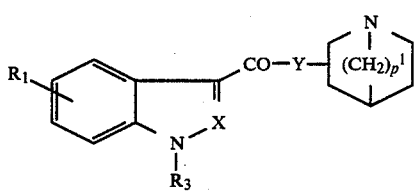

(III)

wherein $p^1$ is 1 or 2 and the remaining variables are as defined in formula (I).

Examples of the variables and preferred variables are as so described for the corresponding variables in formula (I).

There is a further group of compounds within formula (I) of formula (IV):

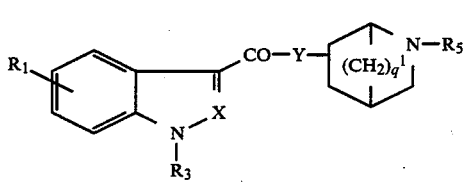

(IV)

wherein $q^1$ is 1 or 2 and the remaining variables are as defined in formula (I).

Examples of the variables and preferred variables are so described as the corresponding variables in formula (I).

The invention also provides a process for the preparation of a compound of formula (I), or a pharmaceutically acceptable salt thereof, which process comprises reacting a compound of formula (V):

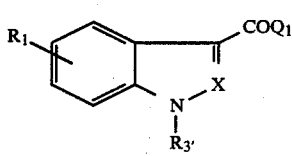

(V)

with a compound of formula (VI):

 (VI)

wherein
$Q_1$ is a leaving group, L is $NH_2$ or OH or a reactive derivative thereof, $R_3'$ is $R_3$ or hydrogen and $R_2$, is $R_2$ wherein $R_4/R_5$ is $R_4/R_5$ or $R_4'/R_5'$ wherein $R_4'/R_5'$ are groups convertible to $R_4/R_5$ and the remaining variables are as hereinbefore defined; and thereafter converting $R_3'$ when hydrogen, to $R_3$, optionally converting any $R_1$, $R_3$, $R_4$, or $R_5$ group to another $R_1$, $R_3$, $R_4$, or $R_5$ group respectively, and optionally forming a pharmaceutically acceptable salt of the resultant compound of formula (I).

Examples of leaving groups $Q_1$, displaceable by a nucleophile, include halogen such as chloro and bromo, hydroxy, carboxylic acyloxy such as $C_{1-4}$ alkanoyloxy or $C_{1-4}$ alkoxycarbonyloxy and activated hydrocarbyloxy such as pentachlorophenoxy. Alternatively, when $R_3'$ is hydrogen and X is N in formula (V), a nitrogen heterocycle may act as the leaving group i.e. that obtained by reaction of a compound of formula (V) wherein Q is OH with thionyl chloride to give a diindazolo[2,3-a,2',3',-d]pyrazine-7,14-dione.

If a group $Q_1$ is a halide, then the reaction is preferably carried out at non-extreme temperatures in an inert non-hydroxylic solvent, such as benzene, dichloromethane, toluene, diethyl ether, THF (tetrahydrofuran) or DMF (dimethylformamide). It is also preferably carried out in the presence of an acid acceptor, such as an organic base, in particular a tertiary amine, such as triethylamine, trimethylamine, pyridine or picoline, some of which can also function as the solvent. Alternatively, the acid acceptor can be inorganic, such as calcium carbonate, sodium carbonate or potassium carbonate. Temperatures of 0°–100° C., in particular 10°–80° C. are suitable.

If a group $Q_1$ is hydroxy, then the reaction is generally carried out in an inert non-hydroxylic solvent, such as dichloromethane, THF or DMF optionally in the presence of a dehydrating catalyst, such as a carbodiimide, for example dicyclohexylcarbodiimide. The reaction may be carried out at any non-extreme temperature, such as $-10°$ to 100° C., for example, 0° to 80° C. Generally, higher reaction temperatures are employed with less active compounds whereas lower temperatures are employed with the more active compounds.

If a group $Q_1$ is carboxylic acyloxy, then the reaction is preferably carried out in substantially the same manner as the reaction when $Q_1$ is halide. Suitable examples of acyloxy leaving groups include $C_{1-4}$ alkanoyloxy and $C_{1-4}$ alkoxycarbonyloxy, in which case the reaction is preferably carried out in an inert solvent, such as methylene chloride, at a non-extreme temperature for example ambient temperatures in the presence of an acid acceptor, such as triethylamine. $C_{1-4}$ alkoxycarbonyloxy leaving groups may be generated in situ by treatment of the corresponding compound wherein $Q_1$ is hydroxy with a $C_{1-4}$ alkyl chloroformate.

If a group $Q_1$ is activated hydrocarbyloxy then the reaction is preferably carried out in an inert polar solvent, such as dimethylformamide. It is also preferred that the activated hydrocarbyloxy group is a pentachlorophenyl ester and that the reaction is carried out at ambient temperature.

When the leaving group $Q_1$ is a nitrogen heterocycle as hereinbefore described the reaction is carried out in a similar manner as when $Q_1$ is a halide.

When L is OH or a reactive derivative thereof, the reactive derivative is often a salt, such as the lithium salt.

Pharmaceutically acceptable salts of the compounds of this invention may be formed conventionally.

The salts may be formed for example by reaction of the base compound of formula (I) with a pharmaceutically acceptable organic or inorganic acid.

When $R_3'$ is hydrogen, it may be converted to $R_3$ when an acyl group by acylation, using an appropriate activated acyl moiety, preferably as an anhydride, such as acetic anhydride, when $R_3$ is acetyl, at ambient temperature in an inert solvent, such as dichloromethane.

For other $R_3$, the conversion of $R_3'$ is hydrogen may be carried out using $R_3Q_2$ wherein $Q_2$ is a leaving group. Suitable values of $Q_2$ are as described hereinbefore as $Q_1$.

For conversion of $R_3'$ is hydrogen when X is CH, it is desirable to carry out the conversion on the sodium or potassium salt, in a solvent such as dimethylformamide.

It will be apparent that compounds of the formula (I) containing an $R_1$ group which is convertible to another $R_1$ group are useful novel intermediates. For example, a hydrogen substituent is convertible to a halogen substituent by halogenation.

$R_4'/R_5'$, when optionally substituted benzyl such as benzyl substituted by one or two halogen, such as chloro and bromo, $C_{1-6}$ alkoxy and $C_{1-6}$ alkyl groups, may be replaced by $R_4/R_5$. Such benzyl groups may, for example, be removed, when $R_1$ is not halogen, by conventional transition metal catalysed hydrogenolysis to give compounds of the formula (VII):

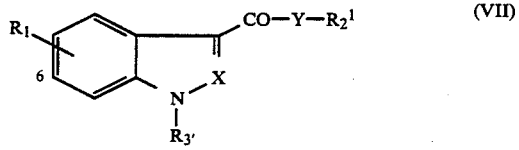

wherein $R_2^1$ is of formula (d) or (e)

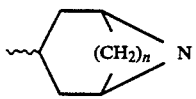

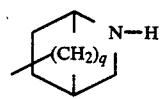

wherein the variables are as defined in formula (I).

This invention also provides a further process for the preparation of a compound of the formula (I) wherein $R_2$ is of formula (a) or (c), which comprises N-alkylating a compound of formula (VII), and optionally forming a pharmaceutically acceptable salt, of the resulting compound of the formula (I).

In this further process of the invention 'N-alkylation' comprises the substitution of the N-atom depicted in formula (VII) by any group $R_4/R_5$ as hereinbefore defined. This may be achieved by reaction of the compound of formula (VII) with a compound $R_4Q_3$ or $R_5Q_3$ wherein $R_4$ and $R_5$ are as hereinbefore defined and $Q_3$ is a leaving group.

Suitable values for $Q_3$ include groups displaced by nucleophiles such as Cl, Br, I, $OSO_2CH_3$ or $OSO_2C_6H_4pCH_3$.

Favoured values for $Q_3$ include Cl, Br and I.

The reaction may be carried out under conventional alkylation conditions, for example in an inert solvent such as dimethylformamide in the presence of an acid acceptor such as potassium carbonate. Generally the reaction is carried out at non-extreme temperature such as at ambient or slightly above.

Alternatively, 'N-alkylation' may be effected under conventional reductive alkylation conditions when the group $R_4$ or $R_5$ in the compound of formula (I) contains a methylene group adjacent to the N-atom in the bicycle.

When $R_4$ or $R_5$ in the compound of formula (VI) contains a methylene group adjacent to the N-atom in the bicycle it is often convenient in the preparation of such a compound of formula (VI) to prepare the corresponding compound wherein the methylene group is replaced by —CO—, or for $R_4$ or $R_5$ is methyl, where the methyl group is replaced by esterified carboxyl. Such compounds may then be reduced using a strong reductant such as lithium aluminium hydride to the corresponding compound of formula (V).

The compounds of formula (V) and (VI) are known or are preparable analogously to, or routinely from, known compounds.

Compounds of the formula (VI) wherein $R_2$ is of formula (c) may be prepared as described in European Patent Publication EP-A-115933 or by analogous methods thereto.

Compounds of the formula (VII) are novel and form an aspect of the invention.

It will be realised that in the compound of the formula (I) the —CO—Y— linkage may have an endo or exo orientation with respect to the ring of the bicyclic moiety to which it is attached. A mixture of endo and exo isomers of the compound of the formula (I) may be synthesised non-stereospecifically and the desired isomer separated conventionally therefrom, e.g. by chromatography; or alternatively the endo isomer may if desired by synthesised from the corresponding isomer of the compound of the formula (VI).

The compounds of the present invention are 5-HT$_3$ antagonists and it is thus believed may generally be used in the treatment or prophylaxis of migraine, cluster headaches and trigeminal neuralgia; and also as antiemetics, in particular that of preventing vomiting and nausea associated with cancer therapy, and motion sickness. Examples of such cancer therapy include that using cytotoxic agents, such as cisplatin, doxorubicin and cyclophosphamide, particularly cisplatin; and also radiation treatment. Compounds which are 5-HT$_3$ antagonists may also be of potential use in the treatment of CNS disorders such as anxiety and psychosis; arrhythmia, obesity and gastro intestinal disorders such as irritable bowel syndrome.

The compounds of the present invention also have gastric motility enhancing activity, useful in the treatment of disorders such as retarded gastric emptying, dyspepsia, flatulence, oesophagal reflux and peptic ulcer.

The invention also provides a pharmaceutical composition comprising a compound of formula (I), or a pharmaceutically acceptable salt thereof, and a pharmaceutically acceptable carrier.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

The oral compositions may be prepared by conventional methods of blending, filling or tabletting. Repeated blending operations may be used to distribute the active agent throughout those compositions employing large quantities of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound of the invention.

The invention further provides a method of treatment or prophylaxis of migraine, cluster headache, trigeminal neuralgia and/or emesis in mammals, such as humans, which comprises the administration to the mammal of an effective amount of a compound of the formula (I) or a pharmaceutically acceptable salt thereof.

An amount effective to treat the disorders hereinbefore described depends on the relative efficacies of the compounds of the invention, the nature and severity of the disorder being treated and the weight of the mammal. However, a unit dose for a 70 kg adult will normally contain 0.5 to 100 mg for example 1 to 500 mg, of the compound of the invention. Unit doses may be administered once or more than once a day, for example, 2, 3 or 4 times a day, more usually 1 to 3 times a day, that is in the range of approximately 0.001 to 50 mg/kg/day, more usually 0.002 to 25 mg/kg/day.

No adverse toxicological effects are indicated at any of the aforementioned dosage ranges.

The invention also provides a compound of formula (I) or a pharmaceutically acceptable salt thereof for use as an active therapeutic substance, in particular for use in the treatment of migraine, cluster headache, trigeminal neuralgia and/or emesis.

The following Examples illustrate the preparation of compounds of formula (I); the following Descriptions relate to the preparation of intermediates.

DESCRIPTION 1

N-(Endo-9-methyl-9-azabicyclo[3.3.1]non-3-yl)acetylindazole-3-carboxamide (D1)

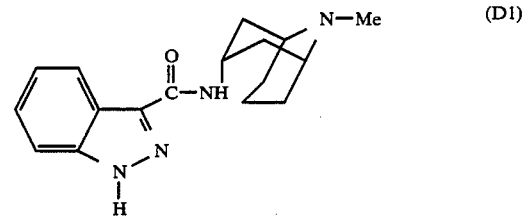

A suspension of diindazolo[2,3-a,2', 3'-]pyrazine-7, 14-dione (0.76 g) in DMF (20 ml) was heated with endo-9-methyl-9-azabicyclo[3.3.1]nonan-3-amine (0.31 g) for 2 h at 100° C. After evaporation to dryness, the residue was purified by column chromatography (TLC grade alumina, CHCl$_3$) to give the title compound (D1) (0.12 g) m.p. 209°–212° C.

| $^1$H NMR (270 MHz, CDCl$_3$) | |
|---|---|
| δ | 13.01 (brs, 1H) |
| | 8.30 (d, 1H) |
| | 7.54 (d, 1H) |
| | 7.35 (t, 1H) |
| | 7.20 (t, 1H) |
| | 7.10 (d, 1H) |
| | 4.54 (dtt, 1H) |
| | 3.12 (brd, 2H) |
| | 2.60–2.40 (m, 5H including 2.53, 2, 3H) |
| | 2.10–1.90 (m, 3H) |
| | 1.60–1.35 (m, 3H) |
| | 1.15–1.00 (m, 2H) |

EXAMPLE 1

(endo)-N-(9-Methyl-9-azabicyclo[3.3.1]nonan-3-yl)-1-acetylindazol-3-yl carboxamide (E1)

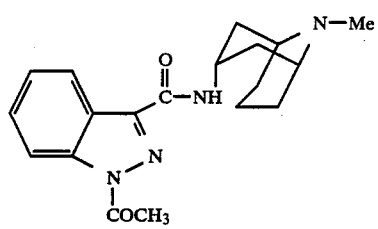

A solution of (endo)-N-(9-methyl-9-azabicyclo[3.3.1]-nonan-3-yl)indazol-3-yl carboxamide (0.3 g) in CH$_2$Cl$_2$ (5 ml) was stirred with acetic anhydride (0.2 ml) for 24 h. The reaction was diluted with CH$_2$Cl$_2$ (50 ml), washed with aqueous NaHCO$_3$ solution (10 ml) and dried (K$_2$CO$_3$). The solvent was evaporated and the residue triturated with ether to give the title compound (E1) (0.2 g) m.p. 167°–9° C.

| $^1$H-NMR ($\delta$, CDCl$_3$) | |
|---|---|
| 8.48–8.39 | (m, 2H) |
| 7.58 | (dt, 1H) |
| 7.44 | (dt, 1H) |
| 6.83 | (brd, 1H) |
| 4.58 | (dtt, 1H) |
| 3.16 | (brd, 2H) |
| 2.82 | (s, 3H) |
| 2.65–2.45 | (m, 5H including 2.53, s, 3H) |
| 2.10–1.90 | (m, 3H) |
| 1.65–1.40 | (m, 3H) |
| 1.10 | (brd, 2H) |

EXAMPLE 2

(endo)-N-(8-methyl-8-azabicyclo[3.2.1.]oct-3-yl)-1-benzoylindazol-3-yl carboxamide monohydrochloride (E2)

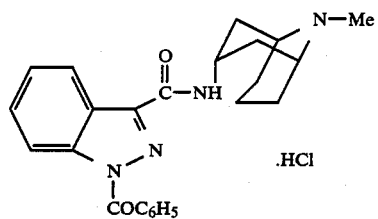

A mixture of (endo)-N-(8-methyl-8-azabicyclo[3.2.1.]-oct-3-yl)indazole-3-yl carboxamide (prepared in an analogous manner to the compound of Description 1) (0.56 g) and benzoyl chloride (0.25 mL) in CH$_2$Cl$_2$ (50 mL) was stirred overnight at room temperature. The reaction was filtered and the filtrate concentrated. Trituration of the residue with Et$_2$O afforded the title compound (0.2 g) m.p. 154°–7° C.

| $^1$H-NMR (d$^6$-DMSO) $\delta$ | |
|---|---|
| 8.53 | (d, 1H) |
| 8.28 | (d, 2H) |
| 8.17 | (d, 2H) |
| 7.73–7.40 | (m, 5H) |
| 4.25–4.16 | (m, 1H) |
| 3.90–3.79 | (brs, 2H) |
| 2.75 | (s, 3H) |
| 2.80–2.60 | (m, 2H) |
| 2.40–2.20 | (m, 6H) |

PHARMACOLOGY

Antagonism of the von Bezold-Jarisch reflex

The compounds were evaluated for antagonism of the von Bezold-Jarisch reflex evoked by 5-HT in the anaesthetised rat according to the following method:

Male rats 250–350 g, were anaesthetised with urethane (1.25 g/kg intraperitoneally) and blood pressure and heart rate recorded as described by Fozard J. R. et al., J. Cardiovasc. Pharmacol. 2, 229–245 (1980). A submaximal dose of 5-HT (usually 6 μg/kg) was given repeatedly by the intravenous route and changes in heart rate quantified. Compounds were given intravenously and the concentration required to reduce the 5-HT-evoked response to 50% of the control response (ED$_{50}$) was then determined.

The compound of Example 1 had an ED$_{50}$ of 2.3 μg/kg.

I claim:

1. A compound of formula (I) or a pharmaceutically acceptable salt thereof:

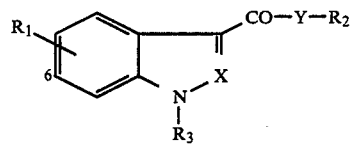

wherein
X is N;
Y is NH;
R$_1$ is hydrogen or halogen;
R$_2$ is a group of formula (a)

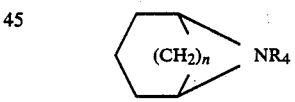

wherein n is 2 or 3;
R$_4$ is C$_{1-4}$ alkyl; and
R$_3$ is C$_{1-10}$ acyl, C$_{1-6}$ alkoxycarbonyl, optionally substituted phenoxycarbonyl or benzyloxycarbonyl, wherein the substituents are selected from C$_{1-4}$ alkyl, C$_{1-4}$ alkoxy, trifluoromethyl, halogen, nitro or C$_{1-6}$ alkylsulphonyl, or R$_6$R$_7$NCO or R$_6$R$_7$NS(O)$_m$ wherein m is 1 or 2 and R$_6$ and R$_7$ are independently C$_{1-6}$ alkyl groups or together are C$_{4-6}$ polymethylene.

2. A compound according to claim 1 wherein R$_1$ is hydrogen or 5-fluoro and R$_4$ is methyl.

3. A compound according to claim 1 wherein R$_3$ is acetyl or benzoyl.

4. A compound selected from (endo)-N-(9-methyl-9azabicyclo[3.3.1]nonan-3-yl)-1-acetylindazol-3-yl carboxamide; (endo)-N-(8-methyl-8-azabicyclo[3.2.1]oct-3-yl)-1-benzoylindazol-3-yl carboxamide or a pharmaceutically acceptable salt thereof.

5. (endo-N-(9-Methyl-9-azabicyclo[3.3.1]nonan-3-yl)-1-acetylindazol-3-yl carboxamide.

6. A compound according to claim 1 wherein the CO—Y— linkage is in the endo configuration with respect to $R_2$.

7. A pharmaceutical composition for use in the treatment of migraine, cluster headache or trigeminal neuralgia, comprising an effective amount of a compound according to claim 1, and a pharmaceutically acceptable carrier.

8. A pharmaceutical composition for use in the treatment of emesis or irritable bowel syndrome, comprising an effective amount of a compound according to claim 1, and a pharmaceutically acceptable carrier.

9. A method of treatment of migraine, cluster headache or trigeminal neuralgia in a mammal, which comprises the administration to a mammal in need thereof of an effective amount of a compound according to claim 1.

10. A method of treatment of emesis or irritable bowel syndrome in a mammal, which comprises the administration to a mammal in need thereof of an effective amount of a compound according to claim 1.

* * * * *